United States Patent
Iizuka

(10) Patent No.: US 8,962,699 B2
(45) Date of Patent: Feb. 24, 2015

(54) LIQUID COMPOSITION TO BE FILLED IN SOFT CAPSULES

(75) Inventor: Masao Iizuka, Osaka (JP)

(73) Assignee: Riken Vitamin Co., Ltd., Tokyo (JP)

( * ) Notice: Subject to any disclaimer, the term of this patent is extended or adjusted under 35 U.S.C. 154(b) by 0 days.

(21) Appl. No.: 13/393,637

(22) PCT Filed: Jun. 14, 2010

(86) PCT No.: PCT/JP2010/060007
§ 371 (c)(1),
(2), (4) Date: Mar. 29, 2012

(87) PCT Pub. No.: WO2011/027605
PCT Pub. Date: Mar. 10, 2011

(65) Prior Publication Data
US 2012/0178830 A1    Jul. 12, 2012

(30) Foreign Application Priority Data
Sep. 7, 2009  (JP) ................. 2009-205731

(51) Int. Cl.
A61K 47/44 (2006.01)
A61K 47/14 (2006.01)
A23L 1/00 (2006.01)
A23L 1/30 (2006.01)
A23L 1/302 (2006.01)
A23L 1/308 (2006.01)
A61K 9/48 (2006.01)

(52) U.S. Cl.
CPC .............. *A61K 47/14* (2013.01); *A23L 1/0032* (2013.01); *A23L 1/3002* (2013.01); *A23L 1/3006* (2013.01); *A23L 1/302* (2013.01); *A23L 1/308* (2013.01); *A61K 9/4858* (2013.01)
USPC ............................. 514/786; 424/400

(58) Field of Classification Search
CPC ... A23L 1/0032; A23L 1/3002; A23L 1/3006; A61K 47/14

USPC ........................... 514/786; 424/400
See application file for complete search history.

(56) References Cited

U.S. PATENT DOCUMENTS

| 6,916,785 B2 * | 7/2005 | Patel ............................. 424/456 |
| 8,075,910 B2 * | 12/2011 | Schramm et al. ............. 424/439 |
| 2002/0099067 A1 * | 7/2002 | Posanski ....................... 514/291 |

FOREIGN PATENT DOCUMENTS

| DE | 4309390 | * 9/1994 | ............ A61K 9/107 |
| WO | 2009/041105 | 4/2009 | |

OTHER PUBLICATIONS

Product description of triglycerol ester, published by Sanansi, China.*
Product properties of CAS #: 59865-13-3, published by ACS.*
Negi DS, title: Base Catalyzed Glycerolysis of Fatty Acid Methyl Esters, Jun. 7, 2006.*
Schneider et al.; machine translation of DE 4309390A1, Sep. 1994.*
English translation of the International Preliminary Report on Patentability and Written Opinion dated Apr. 11, 2012.
International Search Report issued Jul. 20, 2010 in International (PCT) Application No. PCT/JP2010/060007.
Extended European Search Report issued Jun. 17, 2013 in corresponding European Patent Application No. 10813556.7.

* cited by examiner

*Primary Examiner* — Johann R Richter
*Assistant Examiner* — Yanzhi Zhang
(74) *Attorney, Agent, or Firm* — Wenderoth, Lind & Ponack, L.L.P.

(57) ABSTRACT

Disclosed is a liquid composition which is intended to be filled in soft capsules and comprises an oil-insoluble ingredient dispersed in an edible oil, a reactive monoglyceride, and a triglycerol fatty acid ester having a monoester content of 50% or more. The liquid composition to be filled in soft capsules does not comprise bees wax but has a dispersion stability of the oil-insoluble ingredient equal to or higher than that of a conventional composition in which bees wax is used.

6 Claims, No Drawings

LIQUID COMPOSITION TO BE FILLED IN SOFT CAPSULES

This application is a U.S. national stage of International Application No. PCT/JP2010/060007 filed Jun. 14, 2010.

TECHNICAL FIELD

The present invention relates to a liquid composition to be filled in soft capsules.

BACKGROUND ART

Generally, soft capsules comprising an oil-insoluble or powder active ingredient are produced by preparing a dispersion of the active ingredient in an edible oil and filling the dispersion in capsules each having a gelatin coating. In the production, as a dispersant for distributing the active ingredient stably in the edible oil, a glycerol fatty acid ester and bees wax have been conventionally used (see Patent Literature 1).

However, soft capsules in which bees wax is used as the dispersant are known to have a problem; the active ingredient, which can sufficiently disperse in an edible oil, only poorly disperses in vivo after taken into the body, resulting in insufficient effect of the active ingredient. Means for solving the problem, such as a composition in which the active ingredient is suspended by a combination of, for example, a glycerol fatty acid ester and a hydrogenated oil, have been proposed (see Patent Literature 2).

However, the above-mentioned technologies are not necessarily satisfactory from a practical standpoint.

CITATION LIST

Patent Literature

[PTL 1] JP 07-138151 A, paragraph [0019]
[PTL 2] JP 2005-112753 A, paragraph [0020]

SUMMARY OF INVENTION

Technical Problem

An objective of the present invention is to provide a liquid composition to be filled in soft capsules, the composition comprising an oil-insoluble ingredient dispersed in an edible oil, the dispersibility of the oil-insoluble ingredient being equal to or higher than that of a conventional composition in which bees wax is used, both in an edible oil and in vivo.

Solution to Problem

The present inventor has wholeheartedly carried out investigations in order to achieve the objective described above and obtained the following findings.

(i) Use of a reactive monoglyceride as a dispersion stabilizer for dispersing an oil-insoluble ingredient enables the oil-insoluble ingredient, without the aid of bees wax, to be stably dispersed in an edible oil.

(ii) Furthermore, use of a triglycerol fatty acid ester having a monoester content of 50% or more significantly increases the dispersibility of the oil-insoluble ingredient in artificial gastric juice.

The present invention, which has been completed based on the above-mentioned findings, provides the following liquid composition to be filled in soft capsules.

That is, the present invention comprises a liquid composition to be filled in soft capsules, the composition comprising an oil-insoluble ingredient dispersed in an edible oil, a reactive monoglyceride, and a triglycerol fatty acid ester having a monoester content of 50% or more.

Advantageous Effects of Invention

The liquid composition of the present invention to be filled in soft capsules has a dispersion stability of the oil-insoluble ingredient in an edible oil being equal to or higher than that of a conventional composition in which bees wax is used. The liquid composition of the present invention to be filled in soft capsules has a significantly increased dispersibility (dissolution rate) of the oil-insoluble ingredient in artificial gastric juice as compared to that of a conventional composition in which bees wax is used.

DESCRIPTION OF EMBODIMENTS

The liquid composition of the present invention to be filled in soft capsules comprises an oil-insoluble ingredient dispersed in an edible oil with use of a reactive monoglyceride and a triglycerol fatty acid ester having a monoester content of 50% or more.

Edible Oil

The edible oil used in the present invention is not particularly limited as long as it is an edible oil that can be used as a carrier for an oil-insoluble ingredient. Examples of the oil include vegetable oils, such as olive oil, sesame oil, rice oil, safflower oil, soybean oil, corn oil, rapeseed oil, palm oil, palm olein, palm kernel oil, sunflower oil, grapeseed oil, cottonseed oil, coconut oil, and peanut oil; a medium chain triglycerides; squalene; and fish oil. In the present invention, these oils may be used alone or in any combination of two or more kinds.

Oil-Insoluble Ingredient

The oil-insoluble ingredient used in the present invention is composed of a substance with a low lipophilicity and constitutes the active ingredient of the liquid composition of the present invention to be filled in soft capsules. In the present invention, the oil-insoluble ingredient means such an ingredient as follows: when the oil-insoluble ingredient is mixed with an edible oil (for example, safflower salad oil) at a mass ratio of 1:1, the phase comprising the oil-insoluble ingredient and the phase of the edible oil separate from each other.

Examples of the oil-insoluble ingredient include, for example, vitamins (in particular, water soluble vitamins, such as ascorbic acid, vitamins B1, B2, B6, and B12); dietary supplement ingredients, such as citric acid, hyaluronic acid, and calcium powder; health food ingredients, such as royal jelly extract powder, propolis extract powder, blueberry extract powder, agaricus extract powder, shark cartilage extract powder, turmeric extract powder, gingko leaf extract powder, gymnema extract powder, other powders derived from animals and plants, lactose, oligosaccharide, chitosan, and dietary fiber; and medicinal ingredients, such as crude drug extracts, Chinese herbal extracts, and medicinal compositions. Inter alia, blueberry extract powder, gingko leaf extract powder, and vitamins are preferred. These oil-insoluble ingredients may be used alone or in a combination of two or more thereof.

Reactive Monoglyceride

The reactive monoglyceride used in the present invention is a mixture comprising monoglyceride (glycerol monofatty acid ester), diglyceride (glycerol difatty acid ester), and triglyceride (glycerol trifatty acid ester), the mixture being obtainable by removing unreacted glycerol as much as possible from the esterification product of glycerol and fatty acid, or the transesterification product of glycerol and fat (triglyceride). The content of the monoglyceride in the reactive monoglyceride (100%) is usually about 40 to 60%, preferably about 45 to 55%. The content of the diglyceride in the reactive monoglyceride (100%) is usually about 15 to 40%, preferably about 20 to 30%. The content of the triglyceride in the reactive monoglyceride (100%) is usually about 1 to 10%, preferably about 1 to 5%.

The composition of the above reactive monoglyceride, that is, the contents of monoglyceride, diglyceride, and triglyceride in the reactive monoglyceride can be determined by analyzing the reactive monoglyceride by high performance liquid chromatography (HPLC). Specifically, after the reactive monoglyceride is analyzed in the conditions shown below, a chromatogram showing peaks corresponding to each component of the test sample was obtained via a data processing device. Then, peak area measurement for objective peaks is performed with use of an integrator. Based on the measured peak areas, the contents of monoglyceride, diglyceride, and triglyceride can be calculated as area percentage. The HPLC analysis conditions are shown below.

HPLC Analysis Conditions
  Device: High-performance liquid chromatograph (Model: LC-10AS; made by Shimadzu Corp.)
  Detector: RI detector (Model: RID-6A; made by Shimadzu Corp.)
  Column: 2 connected GPC columns (Model: SHODEX KF-802; made by Showa Denko K.K.)
  Column temperature: 40° C.
  Mobile phase: THF
  Flow rate: 1.0 mL/min
  Test liquid injection volume: 15 μL Preferred examples of the fatty acid which constitutes the reactive monoglyceride used in the present invention include straight-chain saturated fatty acids having 6 to 24 carbon atoms derived from edible animal or vegetable oils and fats (for example, caproic acid, caprylic acid, capric acid, lauric acid, myristic acid, palmitic acid, stearic acid, arachidic acid, behenic acid, lignoceric acid, etc.), and more preferred examples include palmitic acid, stearic acid, and behenic acid.

Examples of the production process of the reactive monoglyceride used in the present invention include (1) transesterification of glycerol and fat, and (2) esterification of glycerol and fatty acid. The outlines of the processes are shown in (1) and (2) below.

(1) Production Process of Reactive Monoglyceride by Transesterification

For example, glycerol and fat at the molar ratio of 2:1 are placed into an ordinary reaction container provided with a stirrer, a heating jacket, a baffle plate, etc. To this, for example sodium hydroxide is usually added as a catalyst, and the mixture is stirred and mixed. Under nitrogen atmosphere, the mixture is allowed to react at, for example, about 180 to 260° C., preferably at about 200 to 250° C. for about 0.5 to 15 hours, preferably for about 1 to 3 hours for transesterification. The pressure condition of the reaction is preferably under ordinary pressure or reduced pressure. The obtained reaction liquid is a mixture comprising glycerol, monoglyceride, diglyceride, triglyceride, and the like. After the end of the reaction, the catalyst remaining in the reaction mixture is neutralized, and then preferably the glycerol remaining in the reaction mixture is distilled off by distillation of the reaction mixture under reduced pressure. Subsequently, treatments, such as desalination, decolorization, and filtration are performed if needed to give a reactive monoglyceride comprising about 40 to 60% of monoglyceride relative to the whole.

(2) Production Process of Reactive Monoglyceride by Esterification

For example, glycerol and fatty acid at the molar ratio of 1:1 are placed into an ordinary reaction container provided with a stirrer, a heating jacket, a baffle plate, etc. To this, an acid or an alkali is added as a catalyst if needed, and under an inert gas atmosphere, for example nitrogen atmosphere or carbon dioxide atmosphere, the mixture is allowed to react at, for example, about 180 to 260° C., preferably at about 200 to 250° C. for about 0.5 to 5 hours, preferably for about 1 to 3 hours for esterification. The obtained reaction liquid is a mixture comprising glycerol, monoglyceride, diglyceride, triglyceride, and the like. After the end of the reaction, the catalyst remaining in the reaction mixture is neutralized, and then preferably the glycerol remaining in the reaction mixture is distilled off by distillation of the reaction mixture under reduced pressure. Subsequently, treatments, such as desalination, decolorization, and filtration are performed if needed to give a reactive monoglyceride comprising about 40 to 60% of monoglyceride relative to the whole.

As reactive monoglycerides, for example, Poem P-200 (product name; containing about 52% of monoglyceride; made by Riken Vitamin), Poem V-200 (product name; containing about 50% of monoglyceride; made by Riken Vitamin), Poem B-200 (product name; containing about 47% of monoglyceride; made by Riken Vitamin), etc. are commercially produced and sold. In the present invention, these commercial products can be used as the reactive monoglyceride.

Triglycerol Fatty Acid Ester

The triglycerol fatty acid ester used in the present invention is obtainable by purifying triglycerol fatty acid ester, which is the esterification product of triglycerol and fatty acid, by a method known per se so that the monoester content relative to the whole is increased to about 50% or more. The monoester content relative to the whole is preferably about 70% or more. The upper limit of the monoester content is usually about 96%.

The monoester content in the triglycerol fatty acid ester can be determined by analyzing the triglycerol fatty acid ester by HPLC in the above analysis conditions. Specifically, after the triglycerol fatty acid ester is analyzed in the above HPLC analysis conditions, a chromatogram showing peaks corresponding to each component of the test sample was obtained via a data processing device. Then, peak area measurement for objective peaks is performed with use of an integrator. Based on the measured peak areas, the monoester content can be calculated as area percentage.

Examples of the triglycerol used as a raw material of the triglycerol fatty acid ester used in the present invention include a triglycerol mixture in which the average degree of polymerization of glycerol is about 2.5 to 3.4, preferably about 3.0, the mixture being obtainable by adding a small amount of an acid or an alkali as a catalyst to glycerol, and then heating the mixture under an inert gas atmosphere, for example nitrogen atmosphere or carbon dioxide atmosphere, at a temperature about 180° C. or higher for polycondensation. The triglycerol as a raw material may be obtained using glycidol, epichlorohydrin, or the like as a raw material. After the end of the reaction, treatments, such as neutralization, desalination, and decolorization may be performed if needed.

In the present invention, preferably used is a highly pure triglycerol obtainable by purifying the above triglycerol mixture by a method known per se, for example by distillation or column chromatography, so that the content of triglycerol consisting of three glycerol molecules is increased to about 50% or more, preferably about 85% or more, relative to the whole.

Examples of the fatty acid used as a raw material of the triglycerol fatty acid ester used in the present invention include straight-chain saturated fatty acids having 6 to 24 carbon atoms (for example, caproic acid, caprylic acid, capric acid, lauric acid, myristic acid, palmitic acid, stearic acid, arachidic acid, behenic acid, lignoceric acid, etc.), and straight-chain unsaturated fatty acids having 6 to 24 carbon atoms (for example, palmitoleic acid, oleic acid, elaidic acid, linoleic acid, γ-linolenic acid, α-linolenic acid, arachidonic acid, ricinoleic acid, condensed ricinoleic acid, etc.). Preferred are lauric acid, myristic acid, palmitic acid, stearic acid, oleic acid, and the like. As the fatty acid, fatty acids containing 70% or more of lauric acid, myristic acid, palmitic acid, stearic acid, or oleic acid are commercially available, and such a fatty acid is preferably used in the present invention. Example of the product name of such a fatty acid include, for example, (1) NAA-122 (made by NOF Corp.), (2) Lunac L-98 (made by Kao Corp.), (3) Myristic Acid 98 (made by Miyoshi Oil & Fat Co., Ltd.), (4) NAA-142 (made by NOF Corp.), (5) Lunac MY-98 (made by Kao Corp.), (6) Palmitic Acid 98 (made by Miyoshi Oil & Fat Co., Ltd.), (7) NAA-180 (made by NOF Corp.), (8) Extra Olein (made by NOF Corp.), (9) Lunac O-V (made by Kao Corp.), (10) Lunac O-P (made by Kao Corp.), and the like.

The outline of the preferable production process of the triglycerol fatty acid ester used in the present invention is as follows. For example, triglycerol and fatty acid at the molar ratio of about 1:0.8 to 1:1.2, preferably about 1:1 are placed into an ordinary reaction container provided with a stirrer, a heating jacket, a baffle plate, etc. To this, sodium hydroxide is added as a catalyst, and the mixture is stirred and mixed. Under nitrogen atmosphere, the mixture is kept at a predetermined temperature by heating, during which water generated by the esterification is continuously removed from the system. The reaction temperature is usually within the range of about 180 to 260° C., preferably in the range of about 200 to 250° C. The pressure condition of the reaction is preferably under reduced pressure or ordinary pressure, and the reaction period is about 0.5 to 15 hours, preferably about 1 to 3 hours. The endpoint of the reaction is usually determined by measuring the acid number of the reaction mixture, where about 12 or less is considered to indicate the end point. The obtained reaction liquid is a mixture comprising unreacted fatty acid, unreacted triglycerol, triglycerol monofatty acid ester, triglycerol difatty acid ester, triglycerol trifatty acid ester, triglycerol tetrafatty acid ester, and the like. After the end of the reaction, the obtained reaction liquid is cooled to about 120 to 180° C., preferably about 130 to 150° C. Subsequently, an acid is added to neutralize the catalyst, and the mixture is left to stand for about 15 minutes to 1 hour. Unreacted triglycerol which precipitates in the lower layer, if any, is removed, and triglycerol fatty acid ester is thus obtained.

When the triglycerol fatty acid ester is further purified by molecular distillation using, for example, a falling thin film molecular distillation apparatus or a centrifugal molecular distillation apparatus, or by a method known per se, such as column chromatography or liquid-liquid extraction, a triglycerol fatty acid ester of which the monoester content is about 50% or more, preferably about 70% or more relative to the whole can be obtained.

Other Ingredients

The liquid composition of the present invention to be filled in soft capsules may comprise, as needed, another ingredient in addition to the above-mentioned edible oil, oil-insoluble ingredient, reactive monoglyceride, and triglycerol fatty acid ester of which the monoester content is 50% or more, as long as the effect of the present invention is exerted. Examples of such another ingredient include antioxidants (for example, extracted tocopherol, ascorbyl palmitate). These other ingredients may be used alone or in a combination of two or more kinds thereof.

Preparation Method of the Composition

The liquid composition of the present invention to be filled in soft capsules is produced by dispersing the above-mentioned edible oil, oil-insoluble ingredient, reactive monoglyceride, and triglycerol fatty acid ester with stirring and mixing. Specifically, the composition is produced by, for example, stirring and mixing the edible oil, reactive monoglyceride, and triglycerol fatty acid ester with heating to about 60 to 90° C. for uniform mixing, cooling the mixture down to about 40 to 60° C., adding the oil-insoluble ingredient thereto, and further stirring and mixing for uniform mixing. The reactive monoglyceride and the triglycerol fatty acid ester used here may be a melted mixture thereof prepared beforehand by mixing and heating. The mixing and stirring device is not particularly limited, and for example, a high-speed mixer or a high-speed grinder, such as a biomixer or a homojetter, may be used.

Ingredient Ratio

The edible oil content in 100% by mass of the liquid composition of the present invention to be filled in soft capsules is not particularly limited, and for example, about 20 to 95% by mass, preferably about 20 to 90% by mass, more preferably about 30 to 80% by mass. In the present invention, when the edible oil content is within the above range, the oil-insoluble ingredient can be sufficiently dispersed in the edible oil, and a favorable dispersion stability of the oil-insoluble ingredient in an edible oil can be achieved.

The content of the oil-insoluble ingredient in 100% by mass of the liquid composition of the present invention to be filled in soft capsules is not particularly limited, and for example, about 1 to 70% by mass, preferably about 3 to 60% by mass, more preferably about 10 to 50% by mass. In the present invention, when the content of the oil-insoluble ingredient is within the above range, the oil-insoluble ingredient can be sufficiently dispersed in the edible oil. In addition, since the dispersion stability of the oil-insoluble ingredient in the edible oil is favorable, separation of the oil-soluble ingredient does not occur in soft capsules. Further, since the amount of the active ingredient (oil-insoluble ingredient) in soft capsules is sufficient, the effect of the oil-insoluble ingredient, for example physiological activity, is sufficiently exerted in vivo.

The content of the reactive monoglyceride in 100% by mass of the liquid composition of the present invention to be filled in soft capsules is not particularly limited, and for example, usually about 0.5 to 15% by mass, preferably about 0.5 to 10% by mass, more preferably about 1 to 8% by mass. In the present invention, when the content of the reactive monoglyceride is within the above range, the dispersion stability of the oil-insoluble ingredient in the edible oil is favorable, and separation of the oil-soluble ingredient does not occur in soft capsules. Further, since the amount of the active ingredient (oil-insoluble ingredient) in soft capsules is sufficient, ingestion of the soft capsule brings sufficient effect of the oil-insoluble ingredient in vivo.

In 100% by mass of the liquid composition of the present invention to be filled in soft capsules, the content of the triglycerol fatty acid ester having a monoester content of 50% or more is not particularly limited, and for example, usually about 0.05 to 1.5% by mass, preferably about 0.05 to 1% by mass, more preferably about 0.1 to 1% by mass. In the present invention, when the content of the triglycerol fatty acid ester is within the above range, a favorable dispersion stability of the oil-insoluble ingredient in artificial gastric juice can be achieved in a dispersion test in artificial gastric juice described below. That is, the dispersibility of the oil-insoluble ingredient in vivo is sufficient. Further, since the amount of the active ingredient (oil-insoluble ingredient) in soft capsules is sufficient, ingestion of the soft capsule brings sufficient effect of the oil-insoluble ingredient in vivo. The liquid composition of the present invention to be filled in soft capsules may further comprise other additives, such as a preservative, as needed. However, in terms of sufficient dispersion of the oil-insoluble ingredient, the liquid composition to be filled in soft capsules preferably consists of an edible oil, an oil-insoluble ingredient, a reactive monoglyceride, and a triglycerol fatty acid ester having a monoester content of 50% or more.

Production of Soft Capsules

Soft capsules can be produced by wrapping the thus obtainable liquid composition to be filled in soft capsules, in a coating whose main component is gelatin, by a conventional method. Specifically, for example, the soft capsules can be produced by injecting a certain amount of the liquid composition to be filled in soft capsules between two gelatin sheets followed by punching out.

Dispersion Method of Oil-Insoluble Ingredient

By stirring and mixing a composition comprising an edible oil, an oil-insoluble ingredient, a reactive monoglyceride, and a triglycerol fatty acid ester having a monoester content of 50% or more, the oil-insoluble ingredient can be favorably dispersed in the edible oil. The method for dispersing an oil-insoluble ingredient in an edible oil is also included in the present invention.

The edible oil, oil-insoluble ingredient, reactive monoglyceride, and triglycerol fatty acid ester having a monoester content of 50% or more in the dispersion method of the present invention, and preferred aspects thereof are the same as those in the above description of the liquid composition to be filled in soft capsules. The method for stirring and mixing a composition comprising these ingredients is the same as the method for stirring and mixing the edible oil, oil-insoluble ingredient, reactive monoglyceride, and triglycerol fatty acid ester having a monoester content of 50% or more in the production of the liquid composition to be filled in soft capsules. For example, preferred is uniformly stirring and mixing the edible oil, reactive monoglyceride, and triglycerol fatty acid ester having a monoester content of 50% or more with heating to, for example, about 60 to 90° C., preferably about 70 to 80° C., cooling the mixture down to, for example, about 40 to 60° C., adding the oil-insoluble ingredient thereto, and further stirring and mixing the mixture for uniform mixing.

EXAMPLES

Hereinafter, the present invention will be described in more detail by reference to Examples, but is not limited thereto.

Production Example 1

Into a reaction vessel equipped with a stirrer, a thermometer, a gas blowing pipe, and a water separator, 20 kg of glycerol was placed. To this, 100 mL of a 20 w/v % sodium hydroxide solution was added as a catalyst, and the mixture was kept at 250° C. for 4 hours in nitrogen gas flow for glycerol condensation.

After the obtained reaction product was cooled to about 90° C., neutralization with about 20 g of phosphoric acid (85% by mass) and subsequent filtration were performed. The filtrate was distilled under reduced pressure of 250 Pa at 160° C. for removal of glycerol. Subsequently, molecular distillation was performed under high vacuum of 20 Pa at 200° C. for collection of diglycerol. Molecular distillation of the post-distillation slurry was further performed under high vacuum of 20 Pa at 240° C., and obtained was an about 1.5-kg fraction (triglycerol mixture) comprising 0.2% by mass of glycerol, 5% by mass of diglycerol, 88% of triglycerol, 6% by mass of tetraglycerol, and 0.8% by mass of cyclic glycerol. To the fraction, 1% by mass of activated carbon was added under reduced pressure for decolorization of the mixture, and then filtered out. The hydroxyl value of the obtained triglycerol mixture was about 1170, and the average degree of polymerization thereof was about 3.0.

Production Example 2

Into a 2 L—four-neck flask equipped with a stirrer, a thermometer, a gas blowing pipe, and a water separator, 484 g of triglycerol mixture obtained in the above Production Example 1 and 516 g of palmitic acid (product name: Palmitic Acid 98; made by Miyoshi Oil & Fat Co., Ltd.) were placed. To this, 20 mL of a 10 w/v % sodium hydroxide solution was added as a catalyst, and the mixture was kept at 240° C. for about 2 hours in nitrogen gas flow for esterification until the acid number became equal to or less than 12. The reaction mixture was cooled to about 180° C., 4.6 g of phosphoric acid (85% by mass) was added to neutralize the catalyst, and the mixture was left to stand at the same temperature for about 1 hour. It was confirmed that separation of polyol including unreacted triglycerol was hardly observed. Thus about 960 g of triglycerol palmitate was obtained. Then, the triglycerol palmitate was distilled using a centrifugal molecular distillation apparatus (experimental apparatus; CEH-30011 Special; made by ULVAC). After molecular distillation under vacuum of 20 Pa at about 240° C. for removal of low-boiling compounds, such as unreacted triglycerol, molecular distillation was further continued under vacuum of 1 Pa at about 250° C. As a fraction, about 250 g of triglycerol palmitate having an increased monoester content (Trial Product A; containing about 80% of monoester) was obtained.

Production Example 3

Into a 2 L-four-neck flask with a stirrer, a thermometer, a gas blowing pipe, and a water separator, 510 g of triglycerol mixture obtained in the above Production Example 1 and 490 g of myristic acid (product name: Myristic Acid 98; made by Miyoshi Oil & Fat Co., Ltd.) were placed. To this, 20 mL of a 10 w/v % sodium hydroxide solution was added as a catalyst, and the mixture was kept at 240° C. for about 2 hours in nitrogen gas flow for esterification until the acid number became equal to or less than 12. The reaction mixture was cooled to about 180° C., 4.6 g of phosphoric acid (85% by mass) was added to neutralize the catalyst, and the mixture was left to stand at the same temperature for about 1 hour. It was confirmed that separation of polyol including unreacted triglycerol was hardly observed. Thus about 960 g of triglycerol myristate was obtained. Then, the triglycerol myristate was distilled using a centrifugal molecular distillation apparatus (experimental apparatus; CEH-300II Special; made by ULVAC). After molecular distillation under vacuum of 20 Pa at about 240° C. for removal of low-boiling compounds, such as unreacted triglycerol, molecular distillation was further continued under vacuum of 1 Pa at about 250° C. As a fraction, about 220 g of triglycerol myristate having an increased monoester content (Trial Product B; containing about 75% of monoester) was obtained.

Production Example 4

Into a 2 L-four-neck flask with a stirrer, a thermometer, a gas blowing pipe, and a water separator, 460 g of triglycerol mixture obtained in the above Production Example 1 and 540 g of oleic acid (product name: Oleic Acid V; made by Kao Corp.) were placed. To this, 20 mL of a 10 w/v % sodium hydroxide solution was added as a catalyst, and the mixture was kept at 240° C. for about 2 hours in nitrogen gas flow for esterification until the acid number became equal to or less than 12. The reaction mixture was cooled to about 180° C., 4.6 g of phosphoric acid (85% by mass) was added to neutralize the catalyst, and the mixture was left to stand at the same temperature for about 1 hour. It was confirmed that separation of polyol including unreacted triglycerol was hardly observed. Thus about 960 g of triglycerol oleate was obtained. Then, the triglycerol oleate was distilled using a centrifugal molecular distillation apparatus (experimental apparatus; CEH-300II Special; made by ULVAC). After molecular distillation under vacuum of 20 Pa at about 240° C. for removal of low-boiling compounds, such as unreacted triglycerol, molecular distillation was further continued under vacuum of 1 Pa at about 250° C. As a fraction, about 250 g of triglycerol oleate having an increased monoester content (Trial Product C; containing about 80% of monoester) was obtained.

Production Example 5

Into a 2 L-four-neck flask equipped with a stirrer, a thermometer, a gas blowing pipe, and a water separator, 320 g of triglycerol mixture obtained in the above Production Example 1 and 680 g of palmitic acid (product name: Palmitic Acid 98; made by Miyoshi Oil & Fat Co., Ltd.) were placed. To this, 20 mL of a 10 w/v % sodium hydroxide solution was added as a catalyst, and the mixture was kept at 240° C. for about 2 hours in nitrogen gas flow for esterification until the acid number became equal to or less than 12. The reaction mixture was cooled to about 180° C., and left to stand at the same temperature for about 1 hour. It was confirmed that separation of polyol including unreacted triglycerol was hardly observed. Thus about 960 g of triglycerol palmitate (Trial Product D; containing about 18% of monoester) was obtained.

Example 1

To 60.0 g of safflower salad oil (made by Cargill Japan Ltd.), 7.6 g of reactive monoglyceride (product name: Poem P-200; containing about 52% of monoglyceride; made by Riken Vitamin) and 0.4 g of triglycerol palmitate (Trial Product A) were added, and the mixture was heated to 80° C. with stirring for dissolution. The solution was naturally cooled to 50° C., 1.0 g of riboflavin (made by Riken Vitamin) and 31.0 g of L-ascorbic acid (made by BASF Japan) were added thereto, and the mixture was stirred and mixed with use of a mixer (Model: Ultra Turrax T-25 Basic; made by IKA Japan) at 8000 rpm for 10 minutes. The obtained dispersion liquid was degassed under vacuum and cooled to room temperature. Thus 100 g of a liquid composition to be filled in soft capsules (Practical Product 1) was obtained.

Example 2

In the same manner as in Example 1 except that 0.4 g of triglycerol myristate (Trial Product B) was used instead of 0.4 g of triglycerol palmitate (Trial Product A), 100 g of a liquid composition to be filled in soft capsules (Practical Product 2) was obtained.

Example 3

In the same manner as in Example 1 except that 0.4 g of triglycerol oleate (Trial Product C) was used instead of 0.4 g of triglycerol palmitate (Trial Product A), 100 g of a liquid composition to be filled in soft capsules (Practical Product 3) was obtained.

Comparative Example 1

In the same manner as in Example 1 except that 8.0 g of bees wax (product name: deodorized and purified high-acid value bees wax; made by Cerarica Noda Co., Ltd.) was used instead of 7.6 g of reactive monoglyceride and 0.4 g of triglycerol palmitate (Trial Product A), 100 g of a liquid composition to be filled in soft capsules (Comparative Product 1) was obtained.

Comparative Example 2

In the same manner as in Example 1 except that 4.0 g of beeswax (product name: deodorized and purified high-acid value bees wax; made by Cerarica Noda Co., Ltd.) and 4.0 g of distilled monoglyceride (product name: Poem S-100; containing about 98% of monoglyceride; made by Riken Vitamin) were used instead of 7.6 g of reactive monoglyceride and 0.4 g of triglycerol palmitate (Trial Product A), 100 g of a liquid composition to be filled in soft capsules (Comparative Product 2) was obtained.

Comparative Example 3

In the same manner as in Example 1 except that 0.4 g of triglycerol palmitate (Trial Product D; containing about 18% of monoester) was used instead of 0.4 g of triglycerol palmitate (Trial Product A; containing about 80% of monoester), 100 g of a liquid composition to be filled in soft capsules (Comparative Product 3) was obtained.

<Evaluation of Separation of a Liquid Composition to be Filled in Soft Capsules>

Each of the liquid compositions to be filled in soft capsules prepared as described above (Practical Products 1 to 3 and Comparative Products 1 to 3) was placed, in an amount of 30 g, into a centrifuge tube (capacity: 50 mL; stoppered) and left to stand in an incubator (Model: IN602W; made by Yamato Scientific Co., Ltd.) set at 25° C. for one week. Then, the centrifuge tubes were taken out from the incubator, and the contents of each tube were visually observed for the presence or absence of separated oil-insoluble ingredient (riboflavin and L-ascorbic acid). The results are shown in Table 1.

<Evaluation of Dispersibility of Oil-Insoluble Ingredient in Artificial Gastric Juice>

Into a 200-mL conical flask, 1 g of the liquid composition to be filled in soft capsules (Practical Products 1 to 3 and Comparative Products 1 to 3) and 99 g of artificial gastric juice (1st fluid for dissolution test described in the Japanese Pharmacopoeia 15th Edition; prepared by dissolving 2.0 g of sodium chloride in 7.0 mL of hydrochloric acid and water (q.s. to 1000 mL)) about 36° C. were placed. For mixing and dispersion, the flasks were placed in a bioshaker (Model: BR-23FH; made by Taitec co., Ltd.) at 150 rpm at about 37° C. and shaken for 30 minutes. The obtained dispersion liquid was naturally filtered through a qualitative filter paper No. 2 (125 mm in diameter; made by Advantech) and separated into residue on the paper and filtrate. The obtained filtrate in an amount of 10 g was placed into a petri dish (70 mm in diameter and 50 mm in height) and then dried with hot air in an incubator set at 100° C. for 1 hour. The dry matter remaining on the petri dish was weighed. Based on the weight of the dry matter and the following equation, the dissolution rate (%) of the oil-insoluble ingredient was calculated. The evaluation test was conducted also in cases where the mixing time was 60 minutes or 120 minutes, and the dissolution rates (%) were calculated.

$$\text{Dissolution rate (\%)} = \frac{\text{weight of dry matter (mg)} \times 10 - 198 \text{ (mg)}}{320 \text{ (mg)}} \times 100 \quad \text{[Equation 1]}$$

In the equation, "198" is the weight of NaCl contained in 99 g of the artificial gastric juice, and "320" is the maximum weight of the oil-insoluble ingredient that can be dissolved in 99 g of artificial gastric juice.

TABLE 1

| | Separation of oil-insoluble ingredient | Dissolution rate (%) of oil-insoluble ingredient in artificial gastric juice | | |
|---|---|---|---|---|
| | | Stirred for 30 min | Stirred for 60 min | Stirred for 120 min |
| Practical Product 1 | No | 32.3 | 57.9 | 92.8 |
| Practical Product 2 | No | 40.1 | 58.4 | 89.2 |
| Practical Product 3 | No | 39.4 | 55.2 | 90.3 |
| Comparative Product 1 | Yes | 3.2 | 3.6 | 5.0 |
| Comparative Product 2 | No | 5.0 | 6.3 | 7.8 |
| Comparative Product 3 | No | 7.6 | 13.7 | 20.6 |

As Table 1 clearly shows, Practical Products 1 to 3 exhibited no separation of the insoluble ingredient, and their dissolution rates of the oil-insoluble ingredient in artificial gastric juice were significantly increased as compared to those of conventional compositions in which bees wax is used (Comparative Products 1 and 2). Meanwhile, in the product in which a triglycerol fatty acid ester having a monoester content of less than 50% is used (Comparative Product 3), even though the separation of the oil-insoluble ingredient did not occur, the dissolution rate was not sufficiently improved as compared to those of the compositions in which bees wax is used (Comparative Products 1 and 2).

The invention claimed is:

1. A liquid composition to be filled in soft capsules, the composition comprising an oil-insoluble ingredient dispersed in an edible oil, a reactive monoglyceride, and a triglycerol fatty acid ester, wherein about 40 to 60% of the reactive monoglyceride is monoglyceride, about 15 to 40% of the reactive monoglyceride is diglyceride, about 1 to 10% of the reactive monoglyceride is triglyceride, and 50% or more of the triglycerol fatty acid ester is monoester, and the content of the reactive monoglyceride is about 0.5 to 15% by mass based on total 100% by mass of the liquid composition and the content of the triglycerol fatty acid ester is about 0.05 to 1.5% by mass based on total 100% by mass of the liquid composition.

2. The composition of claim 1, wherein about 45 to 55% of the reactive monoglyceride is monoglyceride, about 20 to 30% of the reactive monoglyceride is diglyceride, and about 1 to 5% of the reactive monoglyceride is triglyceride.

3. The composition of claim 1, wherein about 70% or more of the triglycerol fatty acid ester is monoester.

4. The composition of claim 1, wherein about 70 to 96% of the triglycerol fatty acid ester is monoester.

5. The composition of claim 1, wherein the content of the reactive monoglyceride is about 0.5 to 10% by mass based on total 100% by mass of the liquid composition and the content of the triglycerol fatty acid ester is about 0.05 to 1% by mass based on total 100% by mass of the liquid composition.

6. The composition of claim 1, wherein the content of the reactive monoglyceride is about 1 to 8% by mass based on total 100% by mass of the liquid composition and the content of the triglycerol fatty acid ester is about 0.1 to 1% by mass based on total 100% by mass of the liquid composition.

* * * * *